United States Patent [19]

Otsuka et al.

[11] Patent Number: 4,719,226

[45] Date of Patent: Jan. 12, 1988

[54] PERCUTANEOUS ABSORPTION TYPE PREPARATION AND PROCESS FOR PREPARING THE SAME

[75] Inventors: Saburo Otsuka; Yuusuke Ito; Shoichi Tokuda; Takashi Kinoshita; Keisuke Shibata, all of Osaka, Japan

[73] Assignee: Nitto Electric Industrial Co., Ltd., Osaka, Japan

[21] Appl. No.: 687,898

[22] Filed: Dec. 31, 1984

[30] Foreign Application Priority Data

Mar. 5, 1984 [JP] Japan .................. 59-42641

[51] Int. Cl.[4] .............. A61F 13/00; A61F 13/02; A61F 15/03; A61L 9/70
[52] U.S. Cl. .................. 514/449; 514/447; 514/448
[58] Field of Search .............. 424/28, 32, 34; 514/447, 448, 449

[56] References Cited

U.S. PATENT DOCUMENTS

| | | | |
|---|---|---|---|
| 3,598,122 | 10/1971 | Zaffarone | 424/28 |
| 3,598,123 | 10/1971 | Zaffarone | 428/28 |
| 3,632,740 | 1/1972 | Robinson et al. | 424/34 |

FOREIGN PATENT DOCUMENTS

| | | |
|---|---|---|
| 1577259 | 10/1980 | United Kingdom . |
| 2095108 | 9/1982 | United Kingdom . |
| 2093694 | 9/1982 | United Kingdom . |
| 2140019 | 11/1984 | United Kingdom . |

*Primary Examiner*—Stanley J. Friedman
*Attorney, Agent, or Firm*—Sughrue, Mion, Zinn, Macpeak & Seas

[57] ABSTRACT

A percutaneous absorption type preparation and a process for preparing the same, where the preparation comprises a backing readily conformable to the skin or mucosa and substantially impermeable to a drug absorbed through the skin or mucosa, and an adhesive layer provided on a backing, where the adhesive layer comprises a polymer which is pressure-adhesive at room temperature and the drug present in the polymer, wherein the amount of the drug present in the adhesive layer is greater than its saturated solubility in the polymer is dispersed in the polymer in the form of recrystallized fine particles. The excess portion is again dissolved in the polymer when the drug is consumed as the result of absorption through the skin or mucosa. The drug is released continuously over a long period of time.

10 Claims, No Drawings

PERCUTANEOUS ABSORPTION TYPE PREPARATION AND PROCESS FOR PREPARING THE SAME

FIELD OF THE INVENTION

The present invention relates to a percutaneous absorption type preparation and a process for preparing the preparation. More particularly, it is concerned with a percutaneous absorption type preparation which comprises a backing and an adhesive layer provided on the backing, wherein the adhesive layer comprises a polymer which is pressure-adhesive at room temperature and a drug present in the polymer in the form of recrystallized fine particles and which can be adhered to the skin without any auxiliary means, and a process for preparing the preparation.

BACKGROUND OF THE INVENTION

Many methods have been proposed to administer a percutaneous absorption type drug through the skin. The most typical method comprises forming an adhesive layer comprising a polymer which is pressure-adhesive at room temperature, such as natural rubbers, synthetic rubbers and acryl resins, and a percutaneous absorption type drug dispersed in the polymer on one surface of a flexible backing as disclosed in, for example, U.S. Pat. No. 3,632,740.

The amount of the percutaneous absorption type drug present in those conventional preparations is over a wide range. Usually, however, as disclosed in U.S. Pat. No 3,632,740, particularly the examples therein, the practical amount of the drug present is equal to or below the saturated solubility thereof in the polymer. The reason for this is even if drug is added in an amount greater than the saturated solubility in the polymer, the excess amount above the saturated solubility is present in the polymer in the form of large-sized crystalline particles and thus does not contribute any pharmacological action, viz., it remains on the adhesive layer without being absorbed through the skin.

Several methods have been employed to increase the amount of a drug absorbed through the skin, i.e., the dose of the drug.

One of these methods comprises increasing the thickness of the adhesive layer containing the drug or increasing the size of the preparation. This method, however, is not satisfactory because it is not economical and furthermore gives a feeling of physical discomfort to the user.

As modifications of the above structure, a preparation comprising a backing, an adhesive layer, and a drug reservoir layer (in combination with a drug release rate controlling membrane) is disclosed in, for example, U.S. Pat. Nos. 3,598,122 and 3,598,123. The reservoir layer is composed of a bag or microcapsules with a drug-permeable wall.

The drug present in the reservoir layer is released continuously through the wall, diffuses into the pressure-sensitive adhesive layer adjacent the reservoir layer and is finally administered continuously through the skin or mucosa to which the preparation has been applied. A controlling layer is interposed between the adhesive layer and the reservoir layer and functions to control the release of the drug to the adhesive layer. A preparation of this type has the advantage that the drug can be incorporated regardless of the saturated solubility thereof in the pressure-sensitive adhesive. However, much labor and great costs are required to select the combination of the wall material, the controlling membrane and the drug.

A laminate type preparation comprising a backing layer, a drug reservoir layer, a microporous membrane layer and a contact-adhesive layer, wherein the adhesive layer contains large drug particles in an undissolved state is also disclosed in, for example, U.S. Pat. No. 4,201,211.

The adhesive layer in this preparation is prepared by mixing an inert liquid in which a drug has a low solubility, an adhesive component such as polyisobutylene, and drug particles under conditions such that a high shearing force is exerted on the drug particles to thereby prepare a mixture containing drug particles in a suspended state and then coating the mixture.

In an adhesive layer prepared by coating a liquid containing drug particles suspended in the adhesive component, since the drug particles are not dissolved in the system, the particles are often dispersed non-uniformly in the adhesive layer. As a result, the release of the drug becomes non-uniform. Furthermore, due to the particle size of the drug crystals, it is difficult to form an adhesive layer having a uniform and thin thickness. In particular, the thickness of the adhesive layer cannot be decreased to below the drug particle size since the particles prevent the formation of an adhesive layer having a smooth adhesive layer surface and an adhesive layer, which does not have a smooth layer surface, does not have a satisfactory appearance and also from the standpoint of pharmaceutical effect, the preparation does not have a uniform drug releasing surface.

SUMMARY OF THE INVENTION

Accordingly, one object of the present invention is to provide a percutaneous absorption type preparation having an adhesive layer containing therein a drug in an amount greater than the saturated solubility of the drug in a polymer and where all or a major portion of the drug contributes to the pharmaceutical effect.

Another object of the present invention is to provide a percutaneous absorption type preparation in which a drug is incorporated in the form of specific fine particles formed by crystallization after being dissolved in a polymer so that the preparation contains a large amount of the drug in a thin and small-sized area without the use of an auxiliary means such as a solubility-controlling membrane.

A further object of the present invention is to provide a process for producing a percutaneous absorption type preparation in which a drug is completely dissolved in a polymer in an amount greater than its solubility in the polymer, viz., an excess of the drug is dissolved completely in the polymer so that a uniform and thin adhesive layer is formed and all or a major portion of the drug contributes to the pharmaceutical effect achieved.

The percutaneous absorption type preparation according to the present invention comprises:

(1) a backing which is readily conformable to the surface of the skin or mucosa and which is substantially impermeable to a percutaneous absorption type drug; and (2) an adhesive layer comprising a polymer which is pressure-sensitive at room temperature and the percutaneous absorption type drug (which is solid at room temperature), wherein the drug is present in the adhesive layer in an amount greater than its saturated solubility in the polymer and the drug is dispersed in the polymer in the form of recrystallized fine particles having substantially uniform particle sizes.

The process for preparing the percutaneous absorption type preparation according to the present invention comprises:

(1) dissolving uniformly a polymer which has a pressure-adhesive property at room temperature and a percutaneous absorption type drug in an amount greater than its saturated solubility in the polymer using a good solvent for the polymer and the drug to prepare a coating solution;

(2) coating the coating solution on the surface of a backing which is capable of conforming to the surface of the skin or mucosa and which is substantially impermeable to the drug; and (3) drying the coating solution, wherein excess of the drug present in an amount greater than its saturated solubility in the polymer is recrystallized and dispersed in the polymer in the form of recrystallized fine particles having substantially uniform particle sizes.

DETAILED DESCRIPTION OF THE INVENTION

The term "recrystallized fine particles" as used herein means fine particles formed when a percutaneous absorption type drug, which is solid at room temperature, and a polymer are uniformly and sufficiently dissolved in a good solvent for both the drug and the polymer and the resulting solution is applied to form a coating layer, fine particles of the drug are formed through crystallization and precipitation in the polymer because the drug is present in an amount greater than its saturated solubility in the polymer and have substantially uniform particle sizes. As a result, the fine particles can be dissolved again in the polymer as the dissolved drug is utilized.

The pressure-sensitive properties of a polymer used in the present invention is measured according to a ball tack method wherein a sample having a constant length prepared by coating a polymer on a backing is placed on a slanting surface having an angle of 30° such that the polymer side is upside, a steel ball having 32 kinds of a diameter (1/32 to 1 inch: each is designated as No. 32 to 1, respectively) is fallen down on the sample from a constant height and pressure-sensitive properties of the polymer is expressed as No. of the maximum diameter of the ball which stops on the sample.

The percutaneous absorption type preparation of the present invention has various advantages over the conventional preparations as will hereinafter be explained in detail.

The major advantage of the preparation of this invention is that good release of the drug can be achieved over a long period of time. The reason for this is even though the percutaneous absorption type drug, which is solid at room temperature, is present in a polymer which is pressure-adhesive at room temperature and which constitutes the adhesive layer, in an amount greater than the saturated solubility of the drug in the polymer (preferably not more than about 40% by weight), the amount of the drug in excess of its saturated solubility is recrystallized in the polymer and dispersed in the adhesive layer in the form of fine particles which have substantially uniform particle sizes. As a result, the excess is again dissolved in the polymer as the drug dissolved in the polymer is consumed.

The above-described good drug-releasing effect is beyond that which has generally been accepted in the art to be achievable, that is, a high drug-releasing effect can be obtained when the drug is incorporated in the polymer in an amount equivalent to or less than the saturated solubility of the drug in the polymer. The effect of the present invention has not been disclosed or suggested at all in the prior art relevant to this type of preparations and their similar products.

The present invention is hereinafter explained in greater detail.

The backing provides a self-supporting property to the percutaneous absorption type preparation of the present invention and functions to prevent a decrease in the amount of the drug present through dissipation or migration from the adhesive layer formed on one surface of the backing.

Examples of suitable materials for the backing include films or sheets made of synthetic resins such as polyethylene, polypropylene, polyacrylonitrile, polyurethane, polyester, polyvinyl alcohol, polyvinyl chloride, polyvinylidene chloride, polyamide and ethylene copolymers, which readily conform to the skin or mucosa; laminated films thereof; porous films or sheets made of rubber and/or synthetic resins; fibrous films or sheets such as nonwoven fabrics, fabrics and paper; metallic foils; and the above films or sheets with metal deposited on the surface thereof. The thickness of the backing can be about 500 μm or less, and preferably is from 5 to 150 μm.

The polymer with a pressure-adhesive properties at room temperature (about 20° to 30° C.) is a polymer which can maintain therein a percutaneous absorption type drug in an amount greater than its saturated solubility in the polymer and which forms an adhesive layer from which the drug is administered through the skin or mucosa. Examples of suitable polymers include rubbers and/or synthetic resins, homo-or co-polymers, which are not irritating to the skin or mucosa and do not contain ingredients which affect the drug when mixed therewith, and which exhibit good pressure-adhesive properties. The polymer generally has the pressure-sensitive properties of at least No. 3 measured by the ball tack method as defined before.

It is preferred for the polymer to have a glass transistion temperature ranging between about −10° and about −70° C. If the glass transistion temperature is higher than about −10° C., the polymer is rigid and the diffusion and mobility of the drug in the polymer is reduced, which results in a reduction in release of the drug. Moreover, the dissolution and dispersion of the drug in the polymer during the preparation of the preparation is poor. Further, the re-dissolution of recrystallized fine particles in the preparation is prevented and the drug is not released in a stable manner. On the other hand, if the glass transistion temperature is less than about −70° C., the polymer is undesirably soft and the structure of the preparation is not maintained over a long period of time. When the preparation is peeled from the skin or mucosa, the skin or mucosa is physically irritated and the preparation also remains, e.g., on the skin due to coaggulation or breakage.

It is most preferred for the glass transistion temperature to be from −25° to −50° C.

Examples of suitable polymers which have a glass transistion temperature ranging between about −10° and about −70° C. and which are pressure-adhesive at room temperature include rubbers such as a styrene/isoprene/styrene block copolymer rubber, a styrene/-butadiene rubber, a polybutene rubber, a polyisoprene rubber, a butyl rubber, a silicone rubber, a natural rubber, a synthetic isoprene rubber and the like, and synthetic resins such as poly(meth) acrylate, polyvinyl ether, polyurethane, polyester, polyamide and ethylene copolymers. If desired and necessary, the polymer may contain additives such as a tackifying resin, a liquid rubber, and a softening agent, for example, to control the glass transition temperature.

Polymers which are preferably used in the practice of the present invention are acrylate copolymers containing at least about 50% by weight of acrylic or methacrylic acid alkyl esters and where the average number of carbon atoms in the alkyl group is at least 4. The drug is highly soluble in these copolymers and, the polymers do not irritate the skin or mucosa and maintain the drug in the stable manner.

The above acrylate copolymers include copolymers comprising the acrylic or methacrylic acid ester and functional monomers and/or vinyl ester monomers copolymerizable with the ester. The proportion of the functional monomer can range from 0 to about 20% by weight, preferably from 0.5 to 10% by weight, and the proportion of the vinyl ester monomer can range from 0 to about 40% by weight, preferably from 5 to 30% by weight.

The above functional monomers can be used to change the coagulation properties of the resulting copolymer depending on the amount of the functional monomer employed and also can be used to change the hydrophilic properties of the resulting copolymer depending on the type thereof. The above vinyl ester monomers can be used to increase the solubility of the drug in the copolymer.

Examples of suitable acrylic or methacrylic alkyl esters and functional momomers and vinyl ester monomers are shown below.

Acrylic or methacrylic alkyl esters:

n-butyl acrylate or methacrylate, hexyl acrylate, 2-ethylbutyl acrylate, isooctyl acrylate, 2-ethylhexyl acrylate or methacrylate, nonyl acrylate, decyl acrylate or methacrylate, dodecyl acrylate or methacrylate, tridodecyl acrylate or methacrylate, etc.

Functional monomers:

acrylic or methacrylic acid, itaconic acid, maleic acid, maleic anhydride, hydroxyethyl acrylate, hydroxypropyl acrylate, methoxyethyl acrylate or methacrylate, ethoxyethyl acrylate or methacrylate, butoxyethyl acrylate, acryl or methacrylamide, dimethylacrylamide, dimethylaminoethyl acrylate or methacrylate, tertbutylaminoethyl acrylate or methacrylate, acrylonitrile, vinyl pyrrolidone, vinyl imidazole, etc.

Vinyl ester monomers:

vinyl acetate, vinyl propionate, etc.

Any percutaneous absorption type drugs can be used in the present invention so long as the drugs can be absorbed through the skin into the body when applied onto the skin and are solid at room temperature. Typical examples of such drugs are shown below.

(i) Corticosteroids: hydrocortisone, prednisolone, beclomethasone propionate, flumethasone, triamcinolone, triacinolone acetonide, fluocinolone, fluocinolone acetonide, fluocinolone acetonide acetate, clobetasol proionate, etc.

(ii) Analgesic anti-inflammatory agents: acetaminophen, mefenamic acid, flufenamic acid, indomethacin, diclofenac, dichlofenac sodium alclofenac, oxyphenbutazone, phenylbutazone, ibuprofene, flurbiprofen, salicylic acid, l-menthol, camphor, sulindac tolmetin sodium, naproxen, fenbufen, etc.

(iii) Hypnotic sedatives: phenobarbital, amobarbital, cyclobarbital, triazolam, nitrozepam, lorazepam, holoperidol, etc.

(iv) Tranquilizers: fluphenazine, thioridazine, lorazepam, flunitrazepam, chlorpromazine, etc.

(v) Antihypertensives: clonidine, clonidine hydrochloride, pindolol, propranolol, propranolol hydrochloride, bufralol, indenolol, nipadipine, lofexidine, nipradinol, bucumolol, nifedipine, etc.

(vi) Antihypertensive diuretics: hydrothiazide, bendro-flumethiazide, cyclobenthiazide, etc.

(vii) Antibiotics: penicillin, tetracycline, oxytetracycline, fradiomycin sulfate, erythromycin, chloramphenicol, etc.

(viii) Anesthetics: lidocaine, benzocaine, ethyl aminobenzoate, etc.

(ix) Antimicrobial agents: benzalkonium chloride, nitrofurazone, nystatin, acetosulfamine, clotrimazole, etc.

(x) Antifungal agents: pentamycin, amphotericin B, pyrrolnitrin, clotrimazole, etc.

(xi) Vitamins: vitamin A, ergocalciferol, chlolecalciferol, octotiamine, riboflavine butyrate, etc.

(xii) Antiepileptics: nitrazepam, meprobamate, clonazepam, etc.

(xiii) Coronary vasodilators: nitroglycerin, nitroglycenol, dipyridamole, isosorbide dinitrate, erythritol tetranitrate, pentaerythritol tetranitrate, propatyl nitrate, etc.

(xiv) Antihystaminic agents: diphenylhydramine hydrochloride, chlorpheniramine, diphenylimidazole, etc.

(xv) Antitussire: dertromethorphan (hydrobromide), terbutoline (sulfate), ephedrine (hydrochloride), salbutanol (sulfate), isoproterenol (sulfate, hydrochloride), etc.

(xvi) Sexal hormone: progesterene, estradiol, etc.

(xvii) Thymoleptics: doxepin, etc.

(xviii) Other drugs: 5-fluorouracil, diphydroergotamine (mesytate), fentanyl, desmopressin, digoxin, metochopramide, domperdone, scopalamine (hydrobromide), prostaglandin, peptide, etc.

The amount of the percutaneous absorption type drug added is generally about 40% by weight or less based on the weight of the above polymer. It is preferred that the amount of the percutaneous absorption type drug present be controlled so that the amount is at least 1.2 times, preferably from 1.5 to 10 times, the saturated solubility of the drug in the polymer.

If the amount is less than about 1.2 times, the amount of the recrystallized fine particles in the polymer is too small and the desired drug-releasing effect cannot be obtained.

The percutaneous absorption type drug which is solid at room temperature is added to the polymer which is pressure-adhesive at room temperature in an amount more than its saturated solubility in the polymer and dissolved therein uniformly in the presence of good solvent, so that an adhesive layer can be formed in which part of the drug in an amount equivalent to the saturated solubility is dissolved and the excess is dispersed in the polymer in the form of recrystallized fine particles. The adhesive layer is firmly bound to and fixed to the surface of the backing which is readily conformable to the skin or mucosa and is substantially impermeable to the drug.

The recrystallized fine particles in the adhesive layer which can again dissolve in the polymer are prepared by crystallization and precipitation when the drug is dissolved in the polymer by appropriately selecting a good solvent for both the drug and the polymer. The size of the recrystallized fine particles is about 15 μm or less, preferably from 0.1 to 10 μm.

The thickness of the adhesive layer is from about 5 to about 500 μm, preferably from 10 to 300 μm.

If the thickness of the adhesive layer is less than about 5 m, the adhesiveness of the preparation when applied to the skin is poor. On the other hand, if the thickness is more than about 500 μm, the particle size of recrystallized fine particles is large and not uniform and also the fine particles are not dispersed uniformly. As a result, the drug is not released uniformly.

The percutaneous absorption type preparation of the present invention includes the following embodiments.

One embodiment comprises the adhesive layer on the backing partially shaped in the form of stripes, lattices, and waves, for example. This embodiment includes the embodiment where the adhesive layers comprising polymers having a different glass transition temperature and drugs having a different saturated solubility are alternately formed on the backing or are formed in an island form. This embodiment prevents contact of the skin or mucosa with the air, for example, when the preparation is applied, and permits the rate of release of the drug or the amount of the drug released to be controlled or accelerated.

Another embodiment is one where the amount of the drug in the adhesive layer varies in the thickness direction. More specifically, the adhesive layer is divided into two or more layers and the concentration of the drug in each layer is increased or decreased toward the backing depending on whether it is desired for the pharmaceutical effect to be exhibited slowly or rapidly. If the concentration of the drug in the adhesive layer is increased layer by layer toward the uppermost layer, i.e., the distribution of the recrystallized fine particles and dissolved drug is formed so that the uppermost layer has the highest concentration, by appropriately selecting the type of the good solvent and drying conditions, for example, and increasing the concentration of the drug in the uppermost layer through dissipation of the good solvent, a preparation can be obtained in which the pharmaceutical effect is exhibited quickly and all or major portion of the drug contributes to the pharmaceutical effect. The concentration distribution of the drug is such that the concentration gradient ratio as determined by measuring the concentration in the uppermost layer and the lowermost layer with an infrared spectrum (the reflection method) is about 0.7 or less.

Good solvents which can be used to prepare the percutaneous absorption type preparation of the present invention include organic solvents such as ethyl acetate, chloroform, carbon tetrachloride, methylene chloride, toluene, xylene, tetrahydrofuran, dioxane, acetone, mixtures of the above organic solvents and alcohols such as methyl alcohol and ethyl alcohol, and mixtures of the above mixtures and a small amount (about 5% by weight or less based on the weight of the system) of water.

The polymer and drug are dissolved in a good solvent as described above so that the amount of the drug is at least about 1.2 times the saturated solubility limit thereof in the polymer to thereby prepare a solution for preparation of an adhesive layer having a solids content of from about 10 to about 35% by weight, preferably from 15 to 25% by weight. This solution is coated on a backing in a dry thickness of from about 5 to about 500 μm, preferably from 10 to 300 μm, and dried at about 20° to 150° C. for 3 to 30 minutes. If necessary and required, the coating is further aged for a given period of time. Thus, percutaneous absorption type preparation having an adhesive layer in which the amount of the drug in excess of the saturated solubility limit is recrystallized in the polymer substance and dispersed in the form of recrystallized fine particles having substantially uniform particle sizes (mean particle diameter: about 15 μm or less) can be prepared.

If, after the solution is coated and dried, the resulting coating is pressed or aged in a cooled condition (10° to 30° C.), the precipitation of the recrystallized fine particles is accelerated.

The thus-prepared adhesive layer is provided with a releasing film or its analogous product, the surface of which has been covered with conventional releasing agents such as silicone or fluorine-based releasing agents, so that the adhesive layer is protected until just prior to its use.

If desired, the adhesive layer may contain fillers such as fine silica powder, titanium white and calcium carbonate; absorption accelerating agents such as polyhydric alcohols, sulfoxides, amides, adipates, sebacates, laurates, salicylic acid, urea and allantoin; vehicles such as cyclodextrin and cellulose powder (which are generally mixed with the drug in advance); and compounding agents such as softening agents and anti-itch agents within the range of about 30% by weight or less for the purpose of increasing the volume, accelerating absorption or shape formability.

The adhesive layer in the percutaneous absorption type preparation according to the present invention which comprises a drug and a polymer which is pressure-adhesive at room temperature contains the drug dissolved within the saturated solubility limit in the polymer and the drug as recrystallized and dispersed fine particles which can be redissolved in the polymer. Therefore, the percutaneous absorption type preparation of the present invention has the characteristics that the amount of the drug per unit area is large and the pharmaceutical effect is exhibited continuously over a long period of time since as the amount of the drug dissolved in the polymer is reduced by absorption of the drug through the skin, the remaining drug present in the form of fine particles dissolves again into the polymer and then is absorbed through the skin.

In preparing the preparation of the present invention, a percutaneous absorption type drug and a polymer are thoroughly and uniformly dissolved in a good solvent and then the resulting solution is coated on a support. Therefore, the solution can be coated in a small and uniform thickness and a preparation which has a good appearance and which permits a stable release of the drug can be obtained.

Moreover, the process of the present invention can be employed to produce a percutaneous absorption type preparation which exhibits its pharmaceutical effect continuously over a long period of time by appropriately selecting the good solvent regardless of the saturated solubility of the drug in the polymer.

The present invention is described in greater detail by reference to the following non-limiting examples. All parts are by weight unless otherwise indicated.

EXAMPLE 1

A four-necked separable flask was charged with 94 parts of 2-ethylhexyll acrylate and 6 parts of acrylic acid. In addition, 42.9 parts of ethyl acetate and 0.2 part of azobisisobutyronitrile as a polymerization initiator were added thereto. After heating the mixture to 60° C. in a nitrogen atmosphere, the reaction started. The polymerization reaction was conducted at 60°0 to 62° C. for 7 hours while adding 107.1 parts of ethyl acetate portionwise. The polymerization mixture was further heated and aged for 3 hours. A polymer solution having a conversion of 99.3%, a base content of 30% by weight and the viscosity of 350 poises (at 30° C.) was obtained.

To 80 parts (calculated on a solids basis) of the solution was added 100 parts of ethyl acetate which was a good solvent for the above-prepared polymer and a drug, in which 20 parts of isosorbido dinitrate (the saturated solubility thereof in the above polymer: from about 7 to 8% by weight) had been uniformly dissolved, and the mixture was then stirred to prepare a solution for an adhesive layer.

This solution was coated on a 9 μm thick polyester film in a dry thickness of 50 μm and dried at 90° C. for 5 minutes. A releasing film was then temporarily provided on the above-prepared adhesive layer and the combination was aged at room temperature for 48 hours to produce a percutaneous absorption type preparation.

The releasing film was peeled off and the surface of the adhesive layer was examined with a microscope. This microscopic examination showed that recrystallized fine particles having a mean particle diameter of about 6μ were present on the surface of the adhesive layer. Similarly, the cross section of the adhesive layer was examined and it was found that the concentration of the recrystallized fine particles increased toward the surface layer.

EXAMPLE 2

A composition of 60 parts of nonyl acrylate, 20 parts of ethoxyethyl acrylate and 20 parts of vinyl acetate was polymerized and aged in the same manner as described in Example 1 to prepare a polymer solution having a conversion of 93.3%, a base content of 30% by weight and a viscosity of 285 poises (at 30° C.).

To 90 parts (calculated on a solids basis) of the polymer solution was added 100 parts of ethyl acetate, a good solvent for the polymer and drug, in which 10 parts of flunitrazepam (saturated solubility in the polymer: about 4% by weight) had been uniformly dissolved, and the mixture was stirred to prepare a solution for an adhesive layer.

This solution was coated in a dry thickness of 50 μm on one surface of a 9 μm thick polyester film, the other surface of which had been vacuum deposited aluminum, and then dried at 90° C. for 5 minutes. A releasing film was provided thereon temporarily and the assembly was aged for 2 hours to produce a percutaneous absorption type preparation containing recrystallized fine particles having a mean particle diameter of about 2μ.

EXAMPLE 3

To 90 parts (calculated on a solids basis) of the same polymer solution as prepared in Example 1 was added 50 parts of chloroform, a good solvent for the polymer and drug, in which 10 parts of pindolol (saturated solubility in the polymer: about 4% by weight) had been dissolved uniformly, and the mixture was stirred to prepare a solution for an adhesive layer.

This solution was coated on a heat resistant releasing film in a dry thickness of 40 μm, dried at 100° C. for 5 minutes, bonded under pressure to a two-layer film of polyethylene and an ethylene/vinyl acetate copolymer on the vinyl acetate copolymer side, and then aged at room temperature or ture for 13 days to produce a percutaneous absorption type preparation containing recrystallized fine particles having a mean particle diameter of about 3μ.

EXAMPLE 4

To a commercially available silicone-based pressure-adhesive polymer solution having a non-volatile content (solid content) of 18.5% by weight (Medical Adhesive #355 produced by Dow Corning Co.) was added 60 parts of ethyl acetate, a good solvent for the polymer and a drug, in which 37.5 parts of isosorbide dinitrate-containing milk sugar (isosorbide dinitrate content: 40% by weigh) had been dissolved uniformly, and the mixture was stirred to prepare a solution for an adhesive layer.

This solution was coated on a 9 μm thick polyester film in a dry thickness of 60 μm and dried at 80° C. for 5 minutes. A releasing film was provided thereon temporarily and the combination was aged at room temperature for 24 hours to prepare a percutaneous absorption type preparation containing recrystallized fine particles having a mean particle diameter of about 7μ.

REFERENCE EXAMPLE (A) The polymer solution prepared in Example 2 was concentrated so that the solid content was 60% by weight. To 90 parts (calculated on a solids basis) of the above-concentrated polymer solution was added a dispersion as prepared by uniformly dispersing 10 parts of pindolol in 100 parts of heptane, a poor solvent for pindolol. The resulting mixture was kneaded in a kneader for 1 hour. Thereafter, the mixture was processed in the same manner as described in Example 2 to prepare a percutaneous absorption type preparation. Particles of the drug in the adhesive layer were large particles having a mean particle diameter of about 28μ.

(B) In the same type of silicone-based pressure-adhesive polymer solution as described in Example 4 was uniformly dispersed 37.5 parts of milk sugar containing 40% by weight of isosorbide dinitrate which had not been dissolved in ethyl acetate. Thereafter, the dispersion was processed in the same manner as described in Example 4 to prepare a percutaneous absorption type preparation. Particles of the drug in the adhesive layer were large particles having a mean particle diameter of about 21μ.

The characteristics of the preparations of Examples 1 to 4 and Reference Examples ((A) and (B)) are shown in Table 1 below.

TABLE 1

|  | Adhesiveness to The Skin | Release Ratio in Water (%) | Concentration in Blood (ng/ml) | | | Concentration Gradient Ratio |
| --- | --- | --- | --- | --- | --- | --- |
|  |  |  | 1 hour | 8 hours | 24 hours |  |
| Example 1 | good | 67 | 60 | 330 | 290 | about 0.2 |
| Example 2 | good | 53 | 12 | 24 | 36 | about 0.5 |
| Example 3 | good | 47 | 13 | 43 | 41 | about 0.6 |
| Example 4 | good | 62 | 32 | 280 | 290 | about 0.3 |
| Reference Example A | peeling at the edge | 38 | 4 | 28 | 23 | about 0.9 |
| Reference Example B | peeling at the edge | 51 | 16 | 190 | 170 | about 1.0 |

RELEASE RATIO IN WATER

A test sample (4 cm × 4 cm) was immersed in 500 ml of water maintained at 30° C. and shaken. After 3 hours, 1 ml of the water was sampled and the concentration of the drug was determined by high-speed liquid chromatography (UV detection). The release ratio of the drug was determined with the initial concentration of the drug as 100%.

CONCENTRATION IN BLOOD

A test sample (6 cm in diameter) was adhered to the back of a rabbit where the hair had been removed. After 1 hour, 8 hours and 24 hours, the blood was taken and the concentration of the drug in the blood was measured using gas chromatography.

CONCENTRATION GRADIENT RATIO

The surface infrared spectra of the bottom surface in contact with the backing and the top surface in contact with the releasing film were obtained by the reflective method. In each spectrum, the intensity of a specific peak for the drug was determined. The concentration gradient ratio was calculated from the following equation.

$$\text{Concentration Gradient Ratio} = \frac{\text{Height of specific peak in the spectrum of the bottom surface}}{\text{Height of the specific peak in the spectrum of the top surface}}$$

As the concentration gradient ratio approaches 1, the difference in concentration was small.

While the invention has been described in detail and with reference to specific embodiments thereof, it will be apparent to one skilled in the art that various changes and modifications can be made therein without departing from the spirit and scope thereof.

What is claimed is:

1. A percutaneous absorption type preparation which comprises:
    a backing which is readily conformable to skin or mucosa and is substantially impermeable to a drug absorbed through the skin or mucosa; and
    an adhesive layer provided on the backing, which comprises a polymer which is pressure-adhesive at room temperature, and a drug present in the polymer, wherein the drug is present in the adhesive layer in an amount of at least 1.2 times its saturated solubility in the polymer and the excess amount of the drug greater than the saturated solubility is dispersed in the polymer in the form of recrystallized fine particles having a substantial uniform size, said percutaneous absorption type preparation having been produced by a process comprising the steps of:
    dissolving uniformly a polymer which is pressure-adhesive at room temperature and a percutaneous absorption type drug which is solid at room temperature in an amount of at least 1.2 times its saturated solubility in the polymer in a good solvent to prepare a coating solution having a solids content of from about 10 to about 35% by weight;
    coating the coating solution on the surface of a backing which is conformable to skin or mucosa and is substantially impermeable to the drug;
    drying the coating solution, and recrystallizing and dispersing an amount of the drug greater than its saturated solubility in the polymer in the form of recrystallized fine particles having substantially uniform particle sizes.

2. The preparation as claimed in claim 1, wherein the drug is dispersed in the adhesive so that the concentration of the drug increases toward the top surface of the adhesive layer.

3. The preparation as claimed in claim 1, wherein the recrystallized fine particles have a mean particle diameter of about 15 μm or less.

4. The preparation as claimed in claim 1, wherein the adhesive layer has a thickness of from about 5 to about 500 μm.

5. A process for producing a percutaneous absorption type preparation which comprises:
    dissolving uniformly a polymer which is pressure-adhesive at room temperature and a percutaneous absorption type drug which is solid at room temperature in an amount of at least 1.2 times its saturated solubility in the polymer in a good solvent to prepare a coating solution having a solids content of from about 10 to about 35% by weight.
    coating the coating solution on the surface of a backing which is conformable to skin or mucosa and is substantially impermeable to the drug;
    drying the coating solution, and
    recrystallizing and dispersing an amount of the drug greater than its saturated solubility in the polymer in the form of recrystallized fine particles having substantially uniform particle sizes.

6. The process as claimed in claim 5, wherein the recrystallized fine particles have a mean particle diameter of about 15 μm or less.

7. The preparation as claimed in claim 1, wherein the amount of the drug present in the adhesive layer is 1.5 to 10 time the saturated solubility in the polymer.

8. The preparation as claimed in claim 1, wherein the adhesive layer is prepared by dissolving the drug in the polymer in the presence of a good solvent for the polymer.

9. The process as claimed in claim 5, wherein the amount of the drug present in the adhesive layer is 1.5 to 10 times its saturated solubility in the polymer.

10. A percutaneous absorption type preparation produced by a process comprising the steps of:
dissolving uniformly a polymer which is pressure-adhesive at room temperature and a percutaneous absorption type drug which is solid at room temperature in an amount of at least 1.2 times its saturated solubility in the polymer in a good solvent to prepare a coating solution having a solids content of from about 10 to about 35% by weight;
coating the coating solution on the surface of a backing which is conformable to skin or mucosa and is substantially impermeable to the drug;
drying the coating solution, and recrystallizing and dispersing an amount of the drug greater than its saturated solubility in the polymer in the form of recrystallized fine particles having substantially uniform particle sizes.

* * * * *